United States Patent
Yoda et al.

(10) Patent No.: US 6,891,924 B1
(45) Date of Patent: *May 10, 2005

(54) CONTROL APPARATUS FOR CONTROLLING RADIOTHERAPY IRRADIATION SYSTEM

(75) Inventors: Kiyoshi Yoda, Tokyo (JP); Yukimasa Aoki, Tokyo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/521,217

(22) Filed: Mar. 8, 2000

(30) Foreign Application Priority Data

May 13, 1999 (JP) .......................................... 11-132895

(51) Int. Cl.$^7$ ................................................ A61N 5/10
(52) U.S. Cl. ......................................... 378/65; 378/94
(58) Field of Search ............................ 378/64, 65, 901

(56) References Cited

U.S. PATENT DOCUMENTS

| | | | |
|---|---|---|---|
| 5,291,404 A | | 3/1994 | Kurokawa et al. |
| 5,596,653 A | | 1/1997 | Kurokawa .................. 382/128 |
| 6,038,283 A | * | 3/2000 | Carol et al. .................... 378/65 |
| 6,393,096 B1 | * | 5/2002 | Carol et al. .................... 378/65 |
| 6,459,762 B1 | * | 10/2002 | Wong et al. .................. 378/65 |
| 6,560,311 B1 | * | 5/2003 | Shepard et al. ............... 378/65 |

OTHER PUBLICATIONS

Bortfeld et al.; "Methods of image reconstruction from projections applied to conformation radiotherapy", *Phys. Med. Biol.*, 1990, vol. 35, No. 10, pp. 1423–1434.

Bortfeld et al.; "Clinically Relevant Intensity Modulation Optimization Using Physical Criteria", *XIIth ICCR*, May 27–30, 1997, pp. 1–4.

Bortfeld, Thomas; "Optimized Planning Using Physical Objectives and Constraints", *Seminars in Radiation Oncology*, vol. 9, No. 1, 1999 pp. 20–34.

* cited by examiner

*Primary Examiner*—David V. Bruce
(74) *Attorney, Agent, or Firm*—Leydig, Voit & Mayer, Ltd.

(57) ABSTRACT

A control apparatus for a radiotherapy irradiation system in which a calculation time required for calculation to be performed after restrictions are modified is shortened. The control apparatus includes a unit for setting an initial solution indicating an initial irradiated beam weight, a unit for inputting restrictions according to a prescription, and a unit for setting an evaluation function under the restrictions. The control apparatus further includes a unit for iteratively calculating the evaluation function until the evaluation function is minimized and determining an irradiated beam weight optimizing irradiation, and unit for outputting an optimal solution indicating an optimal irradiated beam weight to the irradiation system. After restrictions are modified, a new evaluation function is set under the modified restrictions. An irradiated beam weight is then determined for optimizing irradiation. At this time, the initial solution setting unit adopts the previous optimal solution indicating an optimal irradiated beam weight, which is obtained before the restrictions are modified, as the initial solution indicating the initial irradiated beam weight.

11 Claims, 6 Drawing Sheets

```
NORMAL TISSUE 10
   MAXIMUM DOSE: 0.33
   VOLUME FRACTION TO RECEIVE MORE THAN
   A NORMALIZED DOSE OF 0.2 : 38%
```

NORMAL TISSUE 10
    MAXIMUM DOSE: 0.24
    VOLUME FRACTION TO RECEIVE MORE THAN
    A NORMALIZED DOSE OF 0.2 : 19%

CONTROL APPARATUS FOR CONTROLLING RADIOTHERAPY IRRADIATION SYSTEM

BACKGROUND OF THE INVENTION

1. Field of the Invention

The present invention relates to a control apparatus for controlling a radiotherapy irradiation system employing X rays and proton beams, which are delivered to a tumor in a human body.

2. Description of the Related Art

Figure 11:
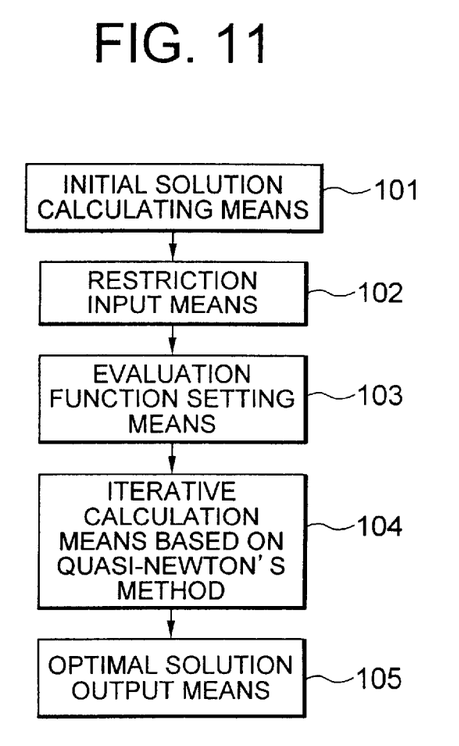
FIG. 11 shows functional blocks of an arithmetic unit included in a conventional control apparatus for a radiotherapy irradiation system, thus describing arithmetic operations performed by the arithmetic unit.

FIG. 11 shows functional blocks of an arithmetic unit included in a conventional control apparatus for controlling a radiotherapy irradiation system proposed by Bortfeld et al. in 1990 (Physics in Medicine and Biology, 1990, Vol. 35, No. 10, pp.1423–1434), thus describing arithmetic operations performed by the arithmetic unit. There are shown an initial solution calculating means 101, a restrictions input means 102, an evaluation function setting means 103, an iterative calculation means based on a quasi-Newton's method 104, and an optimal solution output means 105. These operations are carried out according to a program by means of the arithmetic unit included in the control apparatus for controlling the irradiation system.

Figure 12:
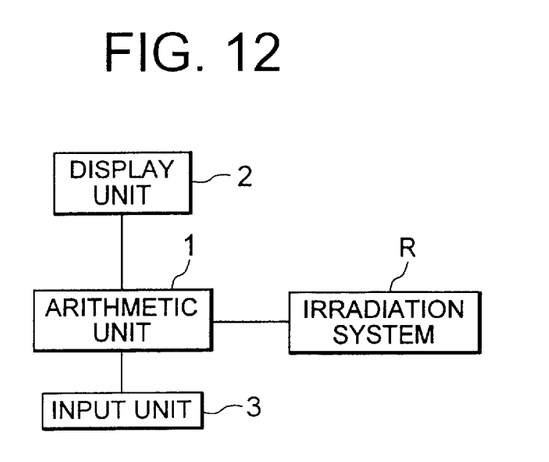
FIG. 12 shows the configuration of this sort of control apparatus for a radiotherapy irradiation system.

FIG. 12 shows the configuration of the above sort of control apparatus for controlling an irradiation system. Shown in FIG. 12 are an arithmetic unit 1, a display unit 2, and an input unit 3. The arithmetic unit 1 performs a series of operations according to a program (not shown). The display unit 2 is realized with a display device or the like. The input unit is realized with a keyboard or mouse. Incidentally, the irradiation system R is an object to which the results of the arithmetic operations are output.

An initial solution is calculated using a projection and reconstruction method devised for the modality of X-ray computed tomography (CT) (101). Thereafter, restrictions are input according to a prescription written out by a radiation oncologist (102). An evaluation function is set under the restrictions (103). Iterative calculation is performed according to a quasi-Newton's method, and an irradiated beam weight is determined for optimizing irradiation (104). An optimal solution indicating the optimal irradiated beam weight is output to the irradiation system R. Consequently, irradiation is carried out optimally. As far as a control apparatus for controlling an irradiation system in reality is concerned, a radiation oncologist observes a distribution of absorbed doses in a human body which is displayed on the display unit 2. The distribution of absorbed doses is obtained through arithmetic operations performed based on the calculated conditions for irradiation. The radiation oncologist then judges whether or not to adopt the conditions for irradiation. If the distribution of absorbed doses in the human body is unsatisfactory, the prescription is modified in order to set new restrictions. An optimal solution indicating an optimal beam weight is calculated under the new restrictions. As the evaluation function, for example, formula (1) is adopted.

$$F(x) = r_0|A(Dx - p_1)|^2 + r_0|B(Dx - p_2)|^2 + \sum_{i=1}^{n} r_i|R(Dx - u)|^2 + \sum_{i=1}^{n} r_i|S(Dx - c)|^2 \quad (1)$$

Now, the first term of the formula (1) expresses a restriction on a minimum dose in a tumor, and the second term thereof expresses a restriction on a maximum dose in the tumor. The third term of the formula (1) expresses a maximum dose in a normal tissue, and the fourth term thereof expresses a restriction on a maximum permitted volume fraction of a normal organ at risk to receive more than a predetermined dose. A coefficient r included in each term is a restriction weight applied relative to each tissue. n denotes the number of normal tissues. According to the quasi-Newton's method, formula (2) is used to perform iterative calculation.

$$\nabla F(x_i) = 2[r_0(AD)^T(ADx - Ap_1) + r_0(BD)^T(BDx - Bp_2) + \sum_{i=1}^{n} r_i(RD)^T(RDx - Ru) + \sum_{i=1}^{n} r_i(SD)^T(SDx - Sc)]$$

$$\nabla^2 F(x) = 2[r_0(AD)^T AD + r_0(BD)^T BD + \sum_{i=1}^{n} r_i(RD)^T RD + \sum_{i=1}^{n} r_i(SD)^T SD]$$

An element of a beam weight vector x giving a negative value is replaced with 0 at every time of iteration, because a beam weight must be 0 or more.

In the conventional control apparatus for controlling the radiotherapy irradiation system, the calculation time required for calculation performed under newly set restrictions is nearly equivalent to the calculation time required for calculation performed under the previous restrictions. Consequently, it takes much time to repeat calculation for different restrictions or prescriptions. Moreover, whether new restrictions are set depends on an operator.

SUMMARY OF THE INVENTION

The present invention attempts to overcome the foregoing drawbacks. An object of the present invention is to minimize the calculation time required for calculation performed under modified restrictions. Another object of the present invention is to automatically judge for each human tissue concerned whether restrictions are satisfied and to automatically modify the restrictions according to the results of judgment.

Accordingly, the present invention provides a control apparatus for controlling a radiotherapy irradiation system comprising an initial solution setting means, a restriction input means, an evaluation function setting means, an iterative calculation means, and an optimal solution output means. The initial solution setting means sets an initial solution indicating an initial irradiated beam weight. The restriction input means inputs restrictions according to a prescription. The evaluation function setting means sets an evaluation function under the restrictions. The iterative calculation means iteratively calculates the evaluation function until the evaluation function is minimized and determines an irradiated beam weight optimizing irradiation. The optimal solution output means outputs an optimal solution indicating an optimal irradiated beam weight to the irradiation system. Herein, the restrictions are modified and a new evaluation function is set under the modified restrictions. An irradiated beam weight is determined for optimizing irradiation. In this case, the initial solution setting means adopts a previous optimal solution indicating an optimal beam weight, which is obtained before the restrictions are modified, as the initial solution indicating the initial irradiated beam weight.

Moreover, the present invention provides a control apparatus for controlling a radiotherapy irradiation system comprising an initial solution setting means, a restriction input means, an evaluation function setting means, an iterative calculation means, and an optimal solution output means. The initial solution setting means sets an initial solution indicating an initial irradiated beam weight. The restriction input means inputs restrictions according to a prescription. The evaluation function setting means sets an evaluation function under the restrictions. The iterative calculation means iteratively calculates the evaluation function until the evaluation function is minimized and determines an irradiated beam weight optimizing irradiation. The optimal solution output means outputs an optimal solution indicating an optimal irradiated beam weight to the irradiation system. The control apparatus further includes a restriction modifying means for judging from a dose distribution, which expresses the distribution of doses in relation to the values of the optimal irradiated beam weight, whether the restrictions are satisfied relative to each human tissue. The restriction modifying means automatically modifies the restrictions when the restrictions are found unsatisfied relative to a human tissue, and instructs optimization of irradiation.

Moreover, in a control apparatus for controlling a radiotherapy irradiation system according to the second aspect of the present invention, after restrictions are modified, when a new evaluation function is set under the modified restrictions, an irradiated beam weight is determined for optimizing irradiation. At this time, the restriction modifying means adopts the previous optimal solution indicating an optimal irradiated beam weight, which is obtained before the restrictions are modified, as the initial solution indicating the initial irradiated beam weight.

Moreover, in a control apparatus for controlling a radiotherapy irradiation system according to any one of the first to third aspects of the present invention, as the restrictions based on a prescription, a maximum absorbed dose and a maximum permitted volume fraction of a normal organ at risk to receive more than a predetermined dose are adopted relative to each normal organ concerned.

Moreover, in a control apparatus for controlling a radiotherapy irradiation system according to any one of the second to fourth aspects of the present invention, the restriction modifying means automatically modifies the restrictions, which are a maximum absorbed dose and a maximum permitted volume fraction of a normal organ at risk to receive more than a predetermined value, when at least one of the restrictions is not satisfied relative to each normal tissue. Thus, both the restrictions, that is, the maximum absorbed dose and a maximum permitted volume fraction of a normal organ at risk to receive more than a predetermined value are modified simultaneously.

Moreover, the present invention provides a control apparatus for controlling a radiotherapy irradiation system comprising an initial solution setting means, a restriction input means, an evaluation function setting means, an iterative calculation means, and an optimal solution output means. The initial solution setting means sets an initial solution indicating an initial irradiated beam weight. The restriction input means inputs restrictions according to a prescription. The evaluation function setting means sets an evaluation function under the restrictions. The iterative calculation means iteratively calculates the evaluation function until the evaluation function is minimized and determines an irradiated beam weight optimizing irradiation. The optimal solution output means outputs an optimal solution indicating an optimal irradiated beam weight to the irradiation system. As one of the restrictions, a restriction weight $r_i$ (i=0,1, . . . ,n) is input relative to each human tissue, where i=0 refers to a tumor while each of i=1, ~n refers to each normal organ at risk. The restriction weight $r_i$ is divided by the volume $V_i$ of the human tissue, and adopted as a new restriction weight. The evaluation function is then calculated.

DESCRIPTION OF THE PREFERRED EMBODIMENTS

Figure 1:
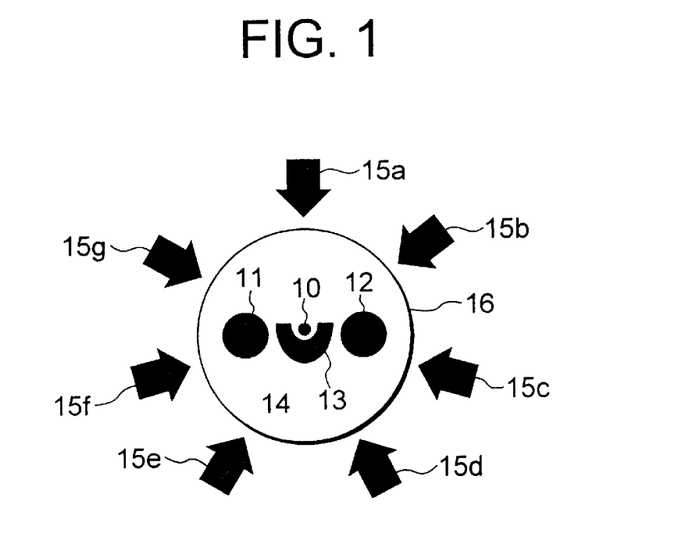
FIG. 1 shows a two-dimensional model representing a section of a human body and an irradiated beam for explaining a control apparatus for controlling a radiotherapy irradiation system in accordance with the present invention.

FIG. 1 shows a two-dimensional model representing a section of a human body and an irradiated beam 15 for explaining a control apparatus for controlling a radiotherapy irradiation system in accordance with the present invention. There are shown normal tissues 10, 11, and 12 and a tumor 13. An area 14 is a remaining area of the section of the human body 16 other than the areas 10, 11, 12 and 13. A radiation beam is irradiated to the tumor in seven directions 15a to 15g. Each irradiation of the radiation beam brings about the one-dimensional distribution of beam weights in a sideways direction. This results in a high dose distribution fitting the contour of any tumor. Moreover, the volume doses at the surrounding normal tissues 10, 11, 12, and 14 are minimized. An actual human body is three-dimensional. Each irradiation of the radiation beam brings about the two-dimensional distribution of beam weights both in the sideways direction and in a direction perpendicular to the drawing paper. Herein, for brevity's sake, a description will be made using the two-dimensional model.

Figure 2:
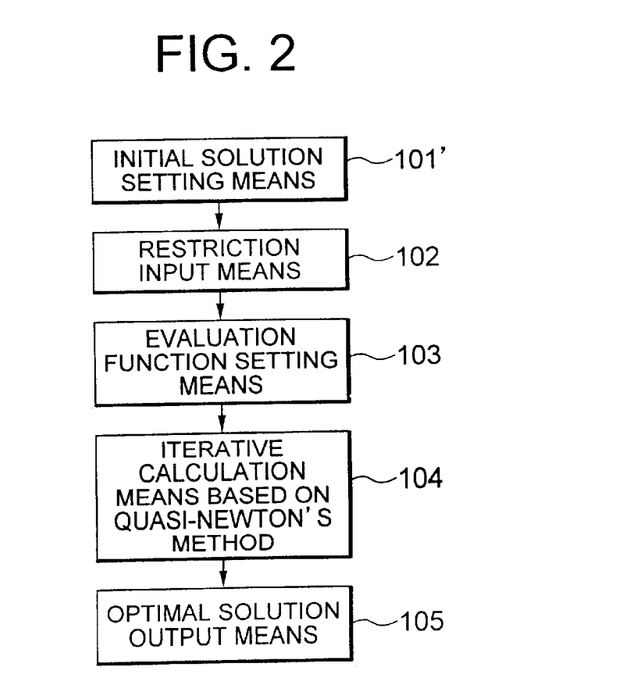
FIG. 2 is a diagram for explaining arithmetic operations concerning the present invention.

FIG. 2 describes arithmetic operations performed by a radiotherapy planning system substantially identical to that shown in FIG. 11. Shown are almost the same functional blocks as those shown in FIG. 11. A different block is an initial solution setting means 101'. In FIG. 11, an initial solution is obtained based on the principles including the principles of the projection and reconstruction method devised for the modality of X-ray CT. According to the present invention, a mere constant (for example, 0 or 1) is employed. Needless to say, the same way of calculation as that described in FIG. 11 may be adopted.

Figure 3:
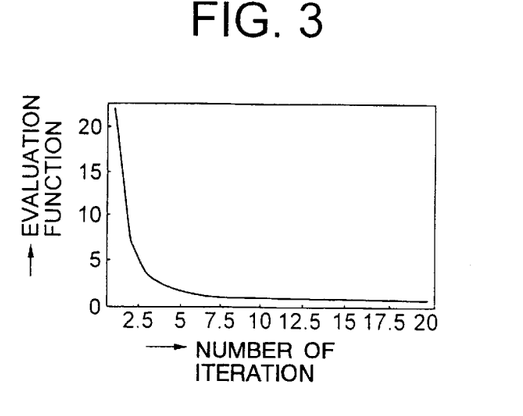
FIG. 3 is a diagram for explaining the trend of an evaluation function being calculated iteratively.
Figure 4A:
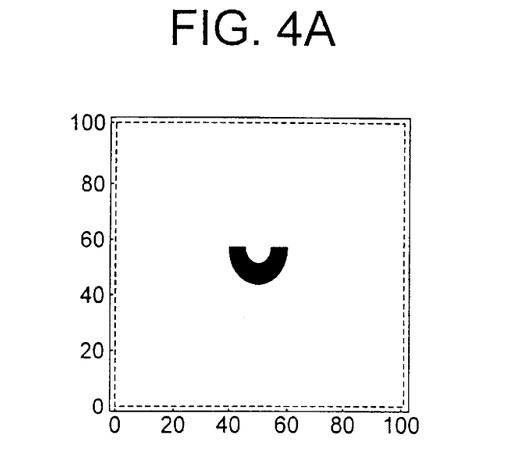
FIG. 4A and FIG. 4B show a dose distribution expressing the distribution of doses in relation to solutions of the evaluation function converged while iteratively calculated which indicate irradiated beam weights.
Figure 4B:
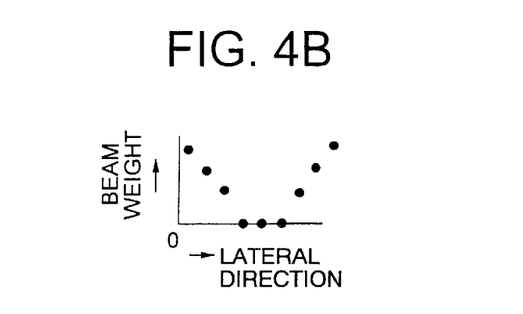
Figure 5:
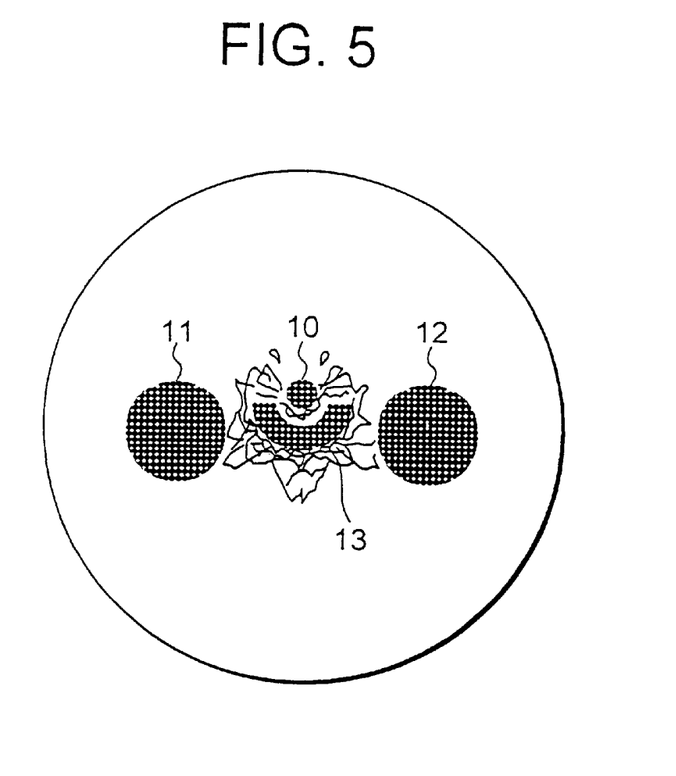
FIG. 5 shows a tumor and normal tissues superimposed by isodose contour lines.

FIG. 3 indicates that an evaluation function decreases during iterative calculation. The evaluation function converges to 0 at the time of the twentieth iteration. FIG. 4A shows an area in which doses indicate 90% or more of an irradiated beam when measured after irradiation performed based on the solution of the evaluation function indicating an irradiated beam weight. FIG. 4B shows some solutions thereof indicating irradiated beam weights. FIG. 5 shows the tumor 13 and the normal tissues 10, 11, and 12 superposed on lines indicating doses equivalent to 40%, 50%, 60%, 70%, 80%, and 90% of an irradiated beam.

Figure 6:
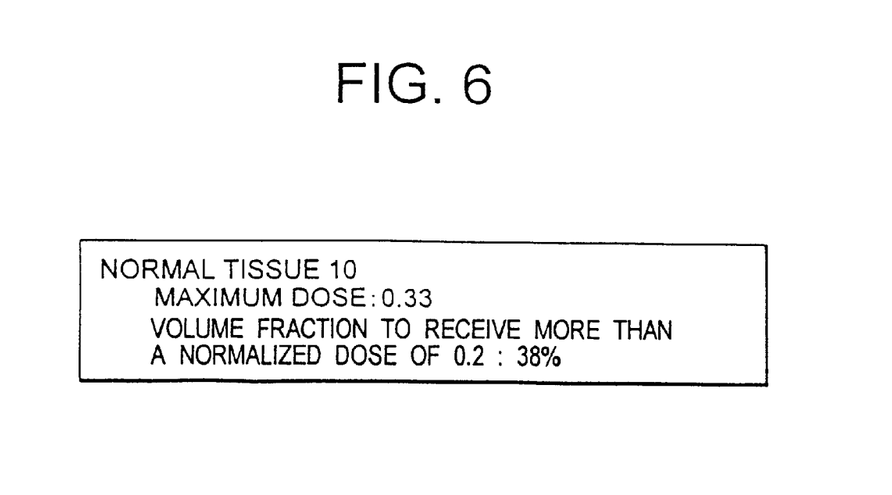
FIG. 6 indicates a maximum dose inside a normal tissue and a volume function to receive more than a predetermined dose.

FIG. 6 indicates a maximum dose in the normal tissue 10 and a volume ratio at which a standardized dose is 0.2 or more. In this case, the maximum standardized dose in the normal tissue 10 is set to 0.33 or less and the volume ratio at which the standardized dose is 0.2 or more is set to 20% or less. The maximum standardized dose and the volume ratio are adopted as restrictions. A measured maximum dose is equal to the set value. However, a measured volume ratio at which the standardized dose is 0.2 or more is 38% or much larger than the target value of 20%.

First Embodiment

Figure 7:
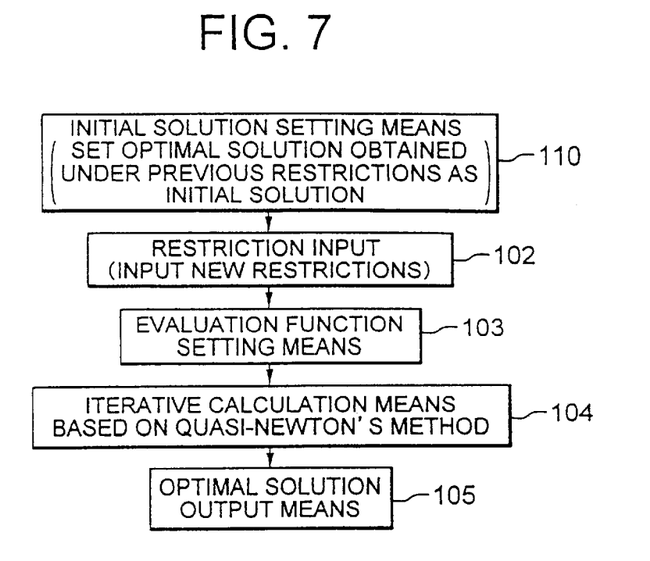
FIG. 7 shows functional blocks of an arithmetic unit included in a control apparatus for controlling a radiotherapy irradiation system in accordance with an embodiment of the present invention, thus describing arithmetic operations performed by the arithmetic unit.
Figure 8:
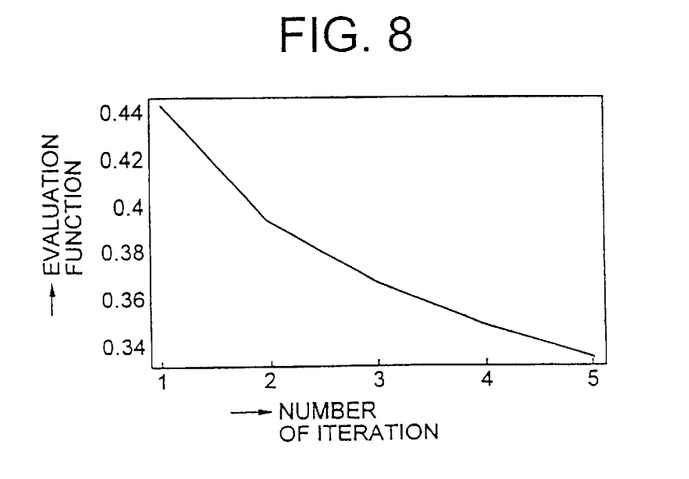
FIG. 8 is a diagram for explaining the trend of an evaluation function being calculated iteratively.
Figure 9:
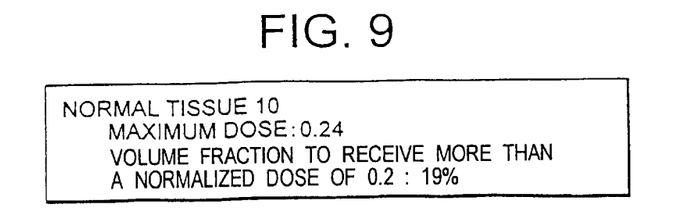
FIG. 9 indicates a maximum dose inside a normal tissue and a volume fraction to receive more than a predetermined dose.

FIG. 7 shows functional blocks of an arithmetic unit included in a control apparatus for a radiotherapy irradiation system in accordance with an embodiment of the present invention. The overall configuration is identical to that shown in FIG. 12. New restrictions are input and calculation for optimization is carried out. The previous solution indicating an optimal irradiated beam weight calculated under the previous restrictions by the initial solution setting means 110 is adopted as an initial solution. The subsequent steps are identical to those in FIG. 2. Consequently, the evaluation function considerably decreases at the time of the fifth iteration as shown in FIG. 8. For this calculation, as the restrictions, the maximum standardized dose in the normal tissue 10 is set to 0.2 or less, and the volume ratio at which the standardized dose is 0.15 or more is set to 20% or less. Consequently, as shown in FIG. 9, a measured maximum dose is 0.24 and a measured volume ratio at which the standardized dose is 0.2 or more is 19%. From this viewpoint, the optimization in accordance with this embodiment has improved compared with the optimization in accordance with the related art.

In this embodiment, for minimizing the volume ratio at which the standardized dose is 0.2 or more, it has proved effective in setting the maximum standardized dose to a stricter and smaller value. The maximum standardized dose correlates with the volume ratio at which the standardized dose is equal to or larger than a predetermined value. Therefore, for minimizing either of the maximum standardized dose and the volume ratio at which the standardized dose is equal to or larger than the predetermined value, both the maximum standardized dose and the volume ratio at which the standardized dose is equal to or larger than the predetermined value should be set to stricter and smaller values and then adopted as restrictions.

Second Embodiment

Figure 10:
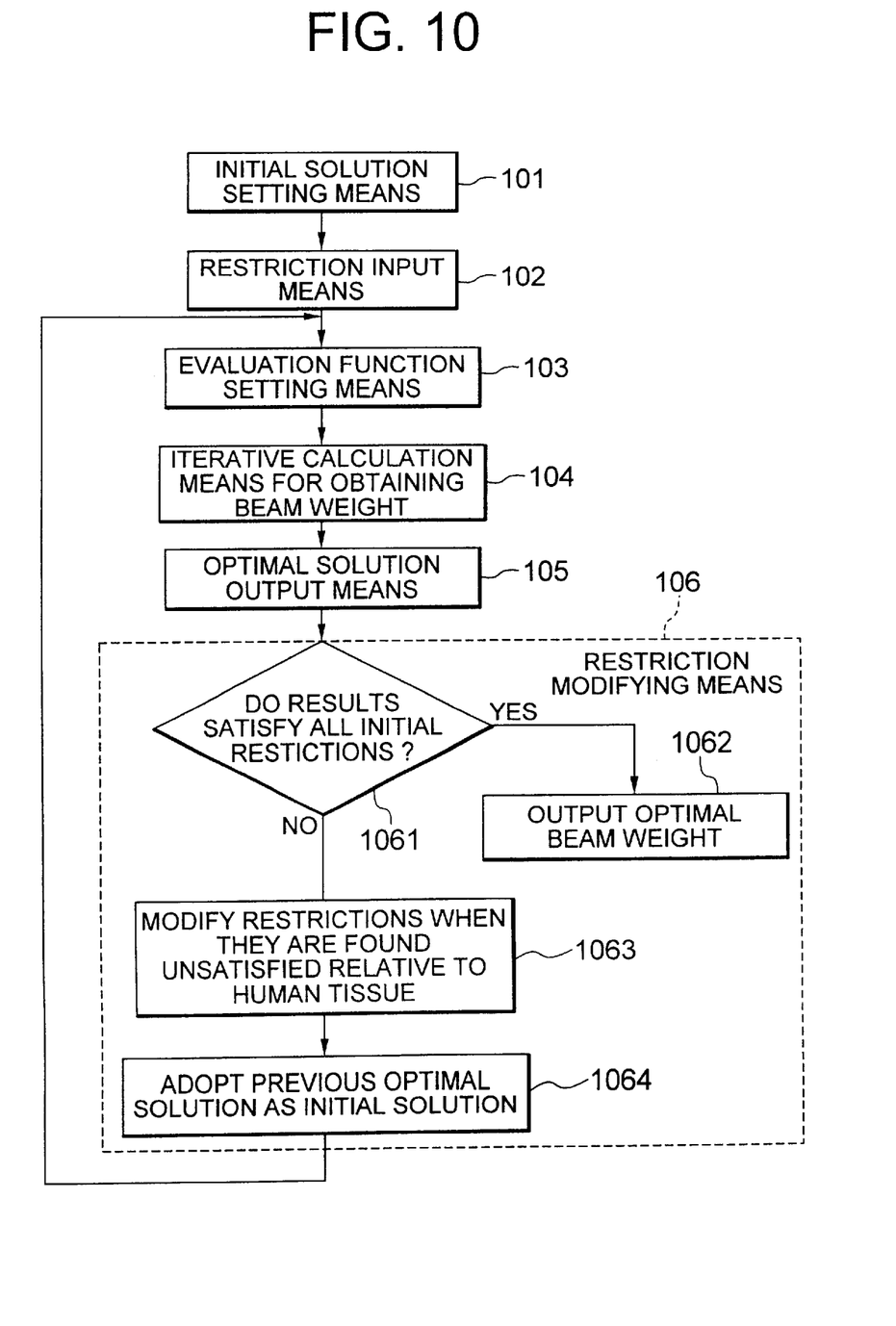
FIG. 10 shows functional blocks of an arithmetic unit included in a control apparatus for controlling a radiotherapy irradiation system in accordance with another embodiment of the present invention, thus describing arithmetic operations performed by the arithmetic unit.

FIG. 10 shows functional blocks of an arithmetic unit included in a control apparatus for a radiotherapy irradiation system in accordance with another embodiment of the present invention, thus describing arithmetic operations performed by the arithmetic unit. The overall configuration is identical to that shown in FIG. 12. A restriction modifying means 106 performs operations 1061 to 1064 so as to satisfy all given restrictions. Moreover, when the restrictions are found unsatisfied relative to a certain human tissue, the restrictions are modified automatically. An optimal solution obtained during the previous optimization is adopted as an initial solution. Consequently, an optimal irradiated beam weight permitting satisfaction of the restrictions can be retrieved efficiently. In reality, a restriction that is set to an unfeasible value remains unsatisfied. Nevertheless, many restrictions can be satisfied.

Even in this embodiment, the maximum standardized dose correlates with the volume ratio at which the standardized dose is equal to or larger than a predetermined value. For minimizing either of them, both of them should be set to stricter and smaller values and adopted as restrictions.

An optimal solution obtained during the previous optimization is adopted as an initial solution at step 1064. This step can be selectively added as an option if necessary.

As the results of various studies, a value input as one of restrictions should not be assigned as the restriction weight $r_i$ (i=0,1, ... ,n) to formula (1) that is the evaluation function (1). Namely, the input value should be divided by a volume $V_i$ of a human tissue concerned and then assigned to the evaluation function (1). For example, assume that the restriction weight is set to $r_0$ relative to a tumor, and to $r_1$ and $r_2$ relative to normal tissues. In this case, the volumes $V_0$, $V_1$, and $V_2$ of the tumor and the normal tissues are calculated, and the restriction weights are divided by the volumes as follows:

$$r_0' = r_0/V_0$$

$$r_1' = r_1/V_1$$

$$r_2' = r_2/V_2$$

The quotients are assigned as the restriction weights $r_0$, $r_1$, and $r_2$ to formula (1). Consequently, when the restriction weight falls within a range of 1 to 10, an irradiated beam weight can be calculated properly relative to a tissue whose volume is large.

When any of values ranging from 1 to 10 is adopted as a restriction weight as it is, the results of evaluation on a tissue having a small volume is ignored almost entirely. An intended irradiated beam weight cannot therefore be obtained (the evaluation function does not converge to 0). For example, assuming that subscript 0 indicates a tumor and subscripts 1 to n indicate normal tissues, $V_0=1000$, $V_1=130$, and $V_2=20000$ are established. In this case, if 1, 5, and 1 are adopted as the restriction weights $r_0$, $r_1$, and $r_2$ respectively as they are, the evaluation function does not decrease to be 10 or less than 10. When the values calculated as follows are assigned as $r_0$, $r_1$, and $r_2$ to formula (1), $$r_0' = r_0/V_0$$

$$r_1' = r_1/V_1$$

$$r_2' = r_2/V_2$$

the evaluation function converges to 1 or less.

As described so far, according to the first aspect of the present invention, there is provided a control apparatus for controlling a radiotherapy irradiation system comprising an initial solution setting means, a restriction input means, an evaluation function setting means, an iterative calculation means, and an optical solution output means. The initial solution setting means sets an initial solution indicating an initial irradiated beam weight. The restriction input means inputs restrictions according to a prescription. The evaluation function setting means sets an evaluation function under the restrictions. The iterative calculation means iteratively calculate the evaluation function until the evaluation function is minimized and determines an irradiated beam weight optimizing irradiation. The optimal solution output means outputs an optimal solution indicating an optimal irradiated beam weight to the irradiation system. Herein, restrictions are modified, and a new evaluation function is set under the modified restrictions. An irradiated beam weight is then determined for optimizing irradiation. At this time, the initial solution setting means adopts the previous optimal solution indicating an optimal irradiated beam weight, which is obtained before the restrictions are modified, as the initial solution indicating the initial irradiated beam weight. Consequently, the calculation time required for calculation performed after the restrictions are modified can be minimized.

Moreover, according to the second aspect of the present invention, there is provided a control apparatus for a control apparatus for controlling a radiotherapy irradiation system comprising an initial solution setting means, a restriction input means, an evaluation function setting means, an iterative calculation means, and an optimal solution output means. The initial solution setting means sets an initial solution indicating an initial irradiated beam weight. The restriction input means inputs restrictions according to a prescription. The evaluation function setting means sets an evaluation function under the restrictions. The iterative calculation means iteratively calculates the evaluation function until the evaluation function is minimized and determines an irradiated beam weight optimizing irradiation. The optimal solution output means outputs an optimal solution indicating an optimal irradiated beam weight to the irradiation system. Herein, the control apparatus further includes a restriction modifying means for judging from a dose distribution, which expresses the distribution of doses in relation to the values of the optimal irradiated beam weight, whether the restrictions are satisfied relative to each human tissue. When the restrictions are not satisfied relative to a human tissue, the restrictions are modified automatically and the irradiation is optimized again. Consequently, whether the restrictions are satisfied is automatically judged relative to each human tissue, and the restrictions can be automatically modified based on the results of judgment.

Moreover, in the second aspect of the present invention, after restrictions are modified, a new evaluation function is set under the modified restrictions, and an irradiated beam weight is determined for optimizing irradiation. At this time, the restriction modifying means adopts the previous optimal solution indicating an optimal irradiated beam weight, which is obtained before the restrictions are modified, as the initial solution indicating the initial irradiated beam weight. Consequently, the restrictions can be modified automatically, and a calculation time required for calculation performed after the restrictions are automatically modified can be shortened.

According to the present invention, as the restrictions based on a prescription, a maximum absorbed dose and a maximum permitted volume fraction of a normal organ at risk to receive more than a predetermined dose are adopted relative to each normal organ concerned. This results in more appropriate radiotherapy.

According to the present invention, the restriction modifying means automatically modifies restrictions, which are a maximum absorbed dose and a maximum permitted volume fraction of a normal organ at risk to receive more than a predetermined dose, when at least one of the restrictions is found unsatisfied relative to a normal tissue. Thus, since both the restrictions that are the maximum absorbed dose and a maximum permitted volume fraction of a normal organ at risk to receive more the volume ratio at which a volume dose is equal to or larger than the predetermined dose are modified simultaneously, more appropriate radiotherapy can be realized.

What is claimed is:

1. A control apparatus for controlling a radiotherapy irradiation system, comprising:

an initial solution setting means for setting an initial solution indicating an initial irradiated beam weight;

restriction input means for inputting restrictions according to a prescription;

evaluation function setting means for setting an evaluation function under the restrictions;

iterative calculation means for iteratively calculating the evaluation function until the evaluation function is minimized and determining an irradiated beam weight optimizing irradiation; and optimal solution output means for outputting an optimal solution indicating an optimal beam weight to the irradiation system, wherein after the restrictions are modified, when setting an evaluation function under modified restrictions and determining an irradiated beam weight for optimizing irradiation, said initial solution setting means adopts the optimal solution indicating an optimal irradiated beam weight, obtained before the restrictions are modified, as an initial solution indicating the initial irradiated beam weight.

2. The control apparatus for controlling a radiotherapy irradiation system according to claim 1, wherein as the restrictions according to a prescription, a maximum absorbed dose and a maximum volume fraction to receive more than a predetermined dose are adopted for each normal tissue.

3. A control apparatus for controlling a radiotherapy irradiation system, comprising:

an initial solution setting means for setting an initial solution indicating an initial irradiated beam weight;

restriction input means for inputting restrictions according to a prescription;

evaluation function setting means for setting an evaluation function under the restrictions;

iterative calculation means for iteratively calculating the evaluation function until the evaluation function is minimized and determining an irradiated beam weight optimizing irradiation;

an optimal solution output means for outputting an optimal solution indicating an optimal irradiated beam weight to the irradiation system; and restriction modifying means for judging from a dose distribution, which expresses or distribution of doses in relation to the optimal irradiated beam weight, whether the restrictions are satisfied relative to each human tissue, automatically modifying the restrictions when the restrictions are found unsatisfied relative to a human tissue, and instructing optimization of irradiation.

4. The control apparatus for controlling a radiotherapy irradiation system according to claim 3, wherein, after modifying the restrictions, when setting a new evaluation function under modified restrictions and determining an irradiated beam weight for optimizing irradiation, said restriction modifying means adopts the optimal solution indicating an optimal irradiated beam weight obtained before the restrictions are modified, as an initial solution indicating the initial irradiated beam weight.

5. The control apparatus for controlling a radiotherapy irradiation system according to claim 3, wherein as the restrictions according to a prescription, a maximum absorbed dose and a maximum volume fraction to receive more than a predetermined dose are adopted for each normal tissue.

6. The control apparatus for controlling a radiotherapy irradiation system according to claim 4, wherein as the restrictions according to a prescription, a maximum absorbed dose and a volume fraction to receive more than a predetermined dose are adopted for each normal tissue.

7. The control apparatus for controlling a radiotherapy irradiation system according to claim 3, wherein said restriction modifying means automatically modifies restrictions, which are a maximum absorbed dose and a maximum volume fraction to receive more than a predetermined dose, when at least one of the restrictions is found unsatisfied relative to a normal tissue, and simultaneously modifies both the restrictions that are the maximum absorbed dose and the maximum volume fraction to more than the predetermined dose.

8. The control apparatus for controlling a radiotherapy irradiation system according to claim 4, wherein said restriction modifying means automatically modifies restrictions, which are a maximum absorbed dose and a volume ratio at which a volume dose is at least equal to a predetermined dose, when at least one of the restrictions is found unsatisfied relative to a normal tissue, and thus simultaneously modifies both restrictions that are the maximum absorbed dose and the maximum volume fraction to more than the predetermined dose.

9. The control apparatus for controlling a radiotherapy irradiation system according to claim 5, wherein said restriction modifying means automatically modifies restrictions, which are a maximum absorbed dose and a volume ratio at which a volume dose is at least equal to a predetermined dose, when at least one of the restrictions is found unsatisfied relative to a normal tissue, and thus simultaneously modifies both restrictions that are the maximum absorbed dose and the maximum volume fraction to more than the predetermined dose.

10. The control apparatus for controlling a radiotherapy irradiation system according to claim 6, wherein said restriction modifying means automatically modifies restrictions, which are a maximum absorbed dose and a maximum volume fraction to receive more than a predetermined dose, when at least one of the restrictions is found unsatisfied relative to a normal tissue, and simultaneously modifies both restrictions that are the maximum absorbed dose and the maximum volume fraction to more than the predetermined dose.

11. A control apparatus for controlling a radiotherapy irradiation system, comprising:
   initial solution setting means for setting an initial solution indicating an initial irradiated beam weight;
   restriction input means for inputting restrictions according to a prescription;
   evaluation function setting means for setting an evaluation function under the restrictions;
   iterative calculation means for iteratively calculating the evaluation function until the evaluation function is minimized and determining an optimal irradiated beam weight optimizing irradiation; and
   optimal solution output means for outputting an optimal solution indicating an optimal irradiated beam weight to said irradiation system,
   wherein a restriction weight $r_i$ (i=0, 1, . . . ,n) to be input as one of the restrictions for each human tissue is divided by volume $V_i$ of the human tissue, and regarded as a new restriction weight in order to calculate the evaluation function, where i=0 refers to a tumor while each of i=1, . . . ,n refers to respective normal organs at risk.

* * * * *